US011103142B2

(12) United States Patent
Tang et al.

(10) Patent No.: US 11,103,142 B2
(45) Date of Patent: Aug. 31, 2021

(54) SYSTEM AND METHOD FOR PREDICTING VERTEBRAL ARTERY DISSECTION

(71) Applicant: TENCENT AMERICA LLC, Palo Alto, CA (US)

(72) Inventors: Hui Tang, Mountain View, CA (US); Nan Du, Santa Clara, CA (US); Min Tu, Cupertino, CA (US); Kun Wang, San Jose, CA (US); Lianyi Han, Palo Alto, CA (US); Wei Fan, New York, NY (US)

(73) Assignee: TENCENT AMERICA LLC, Palo Alto, CA (US)

( * ) Notice: Subject to any disclaimer, the term of this patent is extended or adjusted under 35 U.S.C. 154(b) by 212 days.

(21) Appl. No.: 16/372,996

(22) Filed: Apr. 2, 2019

(65) Prior Publication Data
US 2020/0315465 A1   Oct. 8, 2020

(51) Int. Cl.
| | |
|---|---|
| *A61B 5/02* | (2006.01) |
| *G06T 7/00* | (2017.01) |
| *G06T 7/11* | (2017.01) |
| *G16H 30/40* | (2018.01) |
| *G06N 3/08* | (2006.01) |
| *G06N 3/04* | (2006.01) |
| *G06T 7/174* | (2017.01) |

(Continued)

(52) U.S. Cl.
CPC ........ *A61B 5/02007* (2013.01); *A61B 5/4872* (2013.01); *A61B 5/7267* (2013.01); *A61B 5/7275* (2013.01); *G06N 3/04* (2013.01); *G06N 3/08* (2013.01); *G06T 7/0012* (2013.01); *G06T 7/11* (2017.01); *G06T 7/174*
(2017.01); *G16H 30/40* (2018.01); *G16H 50/30* (2018.01); *G06T 2207/10088* (2013.01); *G06T 2207/20076* (2013.01); *G06T 2207/20081* (2013.01); *G06T 2207/20101* (2013.01); *G06T 2207/30101* (2013.01); *G06T 2207/30172* (2013.01)

(58) Field of Classification Search
USPC .......................................................... 382/128
See application file for complete search history.

(56) References Cited

U.S. PATENT DOCUMENTS

| | | | |
|---|---|---|---|
| 2008/0212857 A1* | 9/2008 | Pfister ....................... | G06T 5/50 382/130 |
| 2009/0043187 A1* | 2/2009 | Lautenschlager ...... | A61B 90/36 600/407 |

(Continued)

OTHER PUBLICATIONS

International Search Report dated May 19, 2020 in PCT/US2020/020091.
Written Opinion dated May 19, 2020 in PCT/US2020/020091.

*Primary Examiner* — Ishrat I Sherali
(74) *Attorney, Agent, or Firm* — Sughrue Mion, PLLC

(57) ABSTRACT

A method of determining a risk probability of vertebral artery dissection (VAD) in a patient, including receiving medical image information of the patient and clinical report information of the patient; extracting at least one biomarker corresponding to a vertebral artery segment included in the medical image information; extracting patient history information from the clinical report information; and determining the risk probability of VAD using a deep learning classification model based on the extracted at least one biomarker and the extracted patient history information.

20 Claims, 8 Drawing Sheets

(51) Int. Cl.
*A61B 5/00* (2006.01)
*G16H 50/30* (2018.01)

(56) References Cited

U.S. PATENT DOCUMENTS

| | | | |
|---|---|---|---|
| 2009/0214097 A1* | 8/2009 | Mohamed | G06T 7/0012 |
| | | | 382/131 |
| 2010/0130878 A1* | 5/2010 | Lasso | G06F 19/00 |
| | | | 600/500 |
| 2012/0323547 A1 | 12/2012 | Baloch et al. | |
| 2013/0022660 A1 | 1/2013 | Macdonald et al. | |
| 2013/0156704 A1* | 6/2013 | Tymianski | A61K 38/10 |
| | | | 424/9.2 |
| 2016/0203288 A1 | 7/2016 | Meng et al. | |
| 2016/0314601 A1* | 10/2016 | Sankaran | G06T 7/20 |
| 2018/0253531 A1* | 9/2018 | Sharma | A61B 6/503 |
| 2018/0315182 A1* | 11/2018 | Rapaka | G16H 50/70 |
| 2020/0118688 A1* | 4/2020 | Pasta | G16H 10/60 |
| 2020/0315547 A1* | 10/2020 | Qian | A61B 5/004 |

* cited by examiner

SYSTEM AND METHOD FOR PREDICTING VERTEBRAL ARTERY DISSECTION

BACKGROUND

Vertebral artery dissection (VAD) is recognized as one of the most frequent causes of transient ischemic attacks and subarachnoid hemorrhage in patients aged between 18 to 45 years old. VAD is easy for clinicians to miss because the associated symptoms are not unusual. As a result, predicting VAD development is important for preventing patients from experiencing VAD and for clinicians to make precise diagnosis and treatment.

Many studies have been conducted to investigate different risk factors for VAD. For example, an investigation into the prevalence of fibromuscular dysplasia in patients with cervical artery dissection (including carotid artery and vertebral artery dissection), found that fibromuscular dysplasia is associated with cervical artery dissection. Another investigation found that aortic root diameter enlargement is associated with an increased risk of spontaneous cervical artery dissection. Recently, vessel wall enhancement and aneurysm dilation have been found to be associated with VAD progression. Increased stiffness of the arterial wall is also found in patients with cervical artery dissection. A review of the risk factors for cervical artery dissection found additional risk factors such as current smoker or not, with or without diabetes and infection.

However, these studies are conducted independently on different groups of patients. There is a need for a system that gathers different risk factors together with information extracted from clinical reports to build a model for predicting the probability of VAD for a subject.

SUMMARY

According to embodiments, a method of determining a risk probability of vertebral artery dissection (VAD) in a patient includes receiving medical image information of the patient and clinical report information of the patient; extracting at least one biomarker corresponding to a vertebral artery segment included in the medical image information; extracting patient history information from the clinical report information; and determining the risk probability of VAD using a deep learning classification model based on the extracted at least one biomarker and the extracted patient history information.

According to embodiments, an apparatus for determining a risk probability of vertebral artery dissection (VAD) in a patient includes at least one memory configured to store program code; and at least one processor configured to read the program code and operate as instructed by the program code, the program code including: receiving code configured to cause the at least one processor to receive medical image information of the patient and clinical report information of the patient; first extracting code configured to cause the at least one processor to extract at least one biomarker corresponding to a vertebral artery segment included in the medical image information; second extracting code configured to cause the at least one processor to extract patient history information from the clinical report information; and determining code configured to cause the at least one processor to determine the risk probability of VAD using a deep learning classification model based on the extracted at least one biomarker and the extracted patient history information.

According to embodiments, a non-transitory computer-readable medium stores instructions that, when executed by at least one processor of a device for determining a risk probability of vertebral artery dissection (VAD) in a patient, cause the at least one processor to receive medical image information of the patient and clinical report information of the patient; extract at least one biomarker corresponding to a vertebral artery segment included in the medical image information; extract patient history information from the clinical report information; and determine the risk probability of VAD using a deep learning classification model based on the extracted at least one biomarker and the extracted patient history information.

DETAILED DESCRIPTION

Embodiments described herein allow prediction of VAD from multi-modality data collected from patients' imaging data, for example time of flight magnetic resonance imaging (MRI) and black blood magnetic resonance angiography (MRA) and clinical reports. These embodiments quantify and gather two types of information: biomarkers from patient's imaging data, such as the geometry of the vertebral arteries, the cervical distortion, stiffness of vessel wall, and information from clinical reports, such as the age, smoking history and medication information of the patient. After quantification of these biomarkers, these embodiment may learn a deep learning model that maps the extracted biomarkers to a risk probability that indicates how likely the patient is to experience VAD in the future.

Embodiments described herein may involve building a model to predict the patient's risk of experiencing VAD. In order to quantify biomarkers from images, the vessel centerline and vessel lumen may be extracted from the images. Because vertebral artery centerlines may be highly curved, for example in the v3 and v4 segments, embodiments may provide an accurate centerline extraction algorithm that works in case of high curviness. For example, embodiments described herein may use a unique centerline refinement step to achieve accurate centerlines even in case of high curviness.

In addition, the vertebral artery lumen is of small size. For example, a lumen of a vertebral artery may have a diameter smaller than 5 mm. In addition, intensity inhomogeneity may occur in the medical images due to an MRI imaging property. Embodiments described herein may segment out the small sized lumen accurately. For example, a deep learning segmentation model may accurately handle mall structure segmentation in the presence of intensity inhomogeneity.

Further, embodiments described herein may also process information from different modalities including MRI images and clinical reports.

Figure 1:
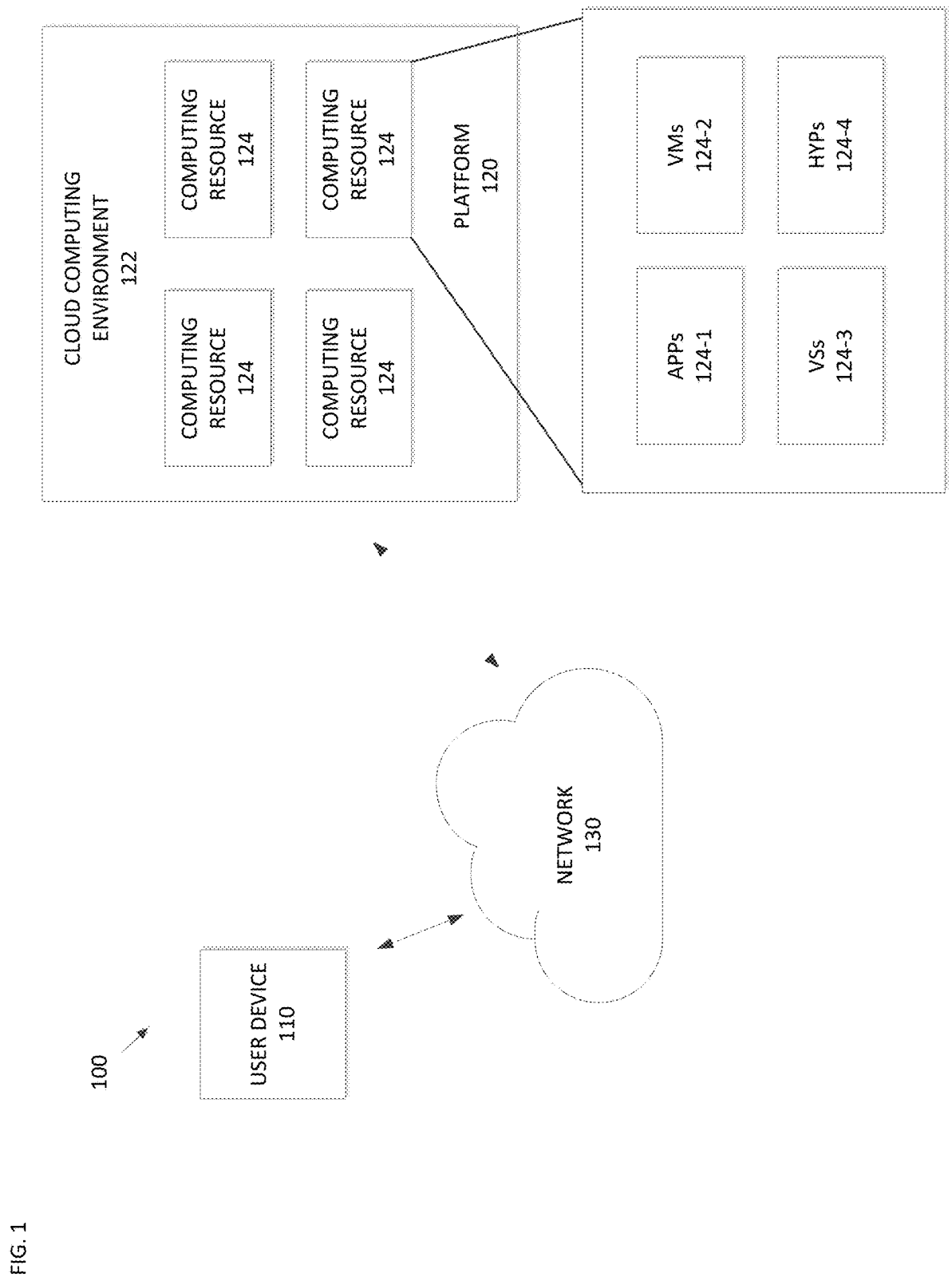
FIG. 1 is a diagram of an environment in which methods, apparatuses and systems described herein may be implemented, according to embodiments.

FIG. 1 is a diagram of an environment 100 in which methods, apparatuses and systems described herein may be implemented, according to embodiments. As shown in FIG. 1, environment 100 may include a user device 110, a platform 120, and a network 130. Devices of environment 100 may interconnect via wired connections, wireless connections, or a combination of wired and wireless connections.

User device 110 includes one or more devices capable of receiving, generating, storing, processing, and/or providing information associated with platform 120. For example, user device 110 may include a computing device (e.g., a desktop computer, a laptop computer, a tablet computer, a handheld computer, a smart speaker, a server, etc.), a mobile phone (e.g., a smart phone, a radiotelephone, etc.), a wearable device (e.g., a pair of smart glasses or a smart watch), or a similar device. In some implementations, user device 110 may receive information from and/or transmit information to platform 120.

Platform 120 includes one or more devices as described elsewhere herein. In some implementations, platform 120 may include a cloud server or a group of cloud servers. In some implementations, platform 120 may be designed to be modular such that software components may be swapped in or out depending on a particular need. As such, platform 120 may be easily and/or quickly reconfigured for different uses.

In some implementations, as shown, platform 120 may be hosted in cloud computing environment 122. Notably, while implementations described herein describe platform 120 as being hosted in cloud computing environment 122, in some implementations, platform 120 is not be cloud-based (i.e., may be implemented outside of a cloud computing environment) or may be partially cloud-based.

Cloud computing environment 122 includes an environment that hosts platform 120. Cloud computing environment 122 may provide computation, software, data access, storage, etc. services that do not require end-user (e.g., user device 110) knowledge of a physical location and configuration of system(s) and/or device(s) that hosts platform 120. As shown, cloud computing environment 122 may include a group of computing resources 124 (referred to collectively as "computing resources 124" and individually as "computing resource 124").

Computing resource 124 includes one or more personal computers, workstation computers, server devices, or other types of computation and/or communication devices. In some implementations, computing resource 124 may host platform 120. The cloud resources may include compute instances executing in computing resource 124, storage devices provided in computing resource 124, data transfer devices provided by computing resource 124, etc. In some implementations, computing resource 124 may communicate with other computing resources 124 via wired connections, wireless connections, or a combination of wired and wireless connections.

As further shown in FIG. 1, computing resource 124 includes a group of cloud resources, such as one or more applications ("APPs") 124-1, one or more virtual machines ("VMs") 124-2, virtualized storage ("VSs") 124-3, one or more hypervisors ("HYPs") 124-4, or the like.

Application 124-1 includes one or more software applications that may be provided to or accessed by user device 110 and/or platform 120. Application 124-1 may eliminate a need to install and execute the software applications on user device 110. For example, application 124-1 may include software associated with platform 120 and/or any other software capable of being provided via cloud computing environment 122. In some implementations, one application 124-1 may send/receive information to/from one or more other applications 124-1, via virtual machine 124-2.

Virtual machine 124-2 includes a software implementation of a machine (e.g., a computer) that executes programs like a physical machine. Virtual machine 124-2 may be either a system virtual machine or a process virtual machine, depending upon use and degree of correspondence to any real machine by virtual machine 124-2. A system virtual machine may provide a complete system platform that supports execution of a complete operating system ("OS"). A process virtual machine may execute a single program, and may support a single process. In some implementations, virtual machine 124-2 may execute on behalf of a user (e.g., user device 110), and may manage infrastructure of cloud computing environment 122, such as data management, synchronization, or long-duration data transfers.

Virtualized storage 124-3 includes one or more storage systems and/or one or more devices that use virtualization techniques within the storage systems or devices of computing resource 124. In some implementations, within the context of a storage system, types of virtualizations may include block virtualization and file virtualization. Block virtualization may refer to abstraction (or separation) of logical storage from physical storage so that the storage system may be accessed without regard to physical storage or heterogeneous structure. The separation may permit administrators of the storage system flexibility in how the administrators manage storage for end users. File virtualization may eliminate dependencies between data accessed at a file level and a location where files are physically stored. This may enable optimization of storage use, server consolidation, and/or performance of non-disruptive file migrations.

Hypervisor 124-4 may provide hardware virtualization techniques that allow multiple operating systems (e.g., "guest operating systems") to execute concurrently on a host computer, such as computing resource 124. Hypervisor 124-4 may present a virtual operating platform to the guest operating systems, and may manage the execution of the guest operating systems. Multiple instances of a variety of operating systems may share virtualized hardware resources.

Network 130 includes one or more wired and/or wireless networks. For example, network 130 may include a cellular network (e.g., a fifth generation (5G) network, a long-term evolution (LTE) network, a third generation (3G) network, a code division multiple access (CDMA) network, etc.), a public land mobile network (PLMN), a local area network (LAN), a wide area network (WAN), a metropolitan area network (MAN), a telephone network (e.g., the Public Switched Telephone Network (PSTN)), a private network, an ad hoc network, an intranet, the Internet, a fiber optic-based network, or the like, and/or a combination of these or other types of networks.

The number and arrangement of devices and networks shown in FIG. 1 are provided as an example. In practice, there may be additional devices and/or networks, fewer devices and/or networks, different devices and/or networks, or differently arranged devices and/or networks than those shown in FIG. 1. Furthermore, two or more devices shown in FIG. 1 may be implemented within a single device, or a single device shown in FIG. 1 may be implemented as multiple, distributed devices. Additionally, or alternatively, a set of devices (e.g., one or more devices) of environment 100 may perform one or more functions described as being performed by another set of devices of environment 100.

Figure 2:
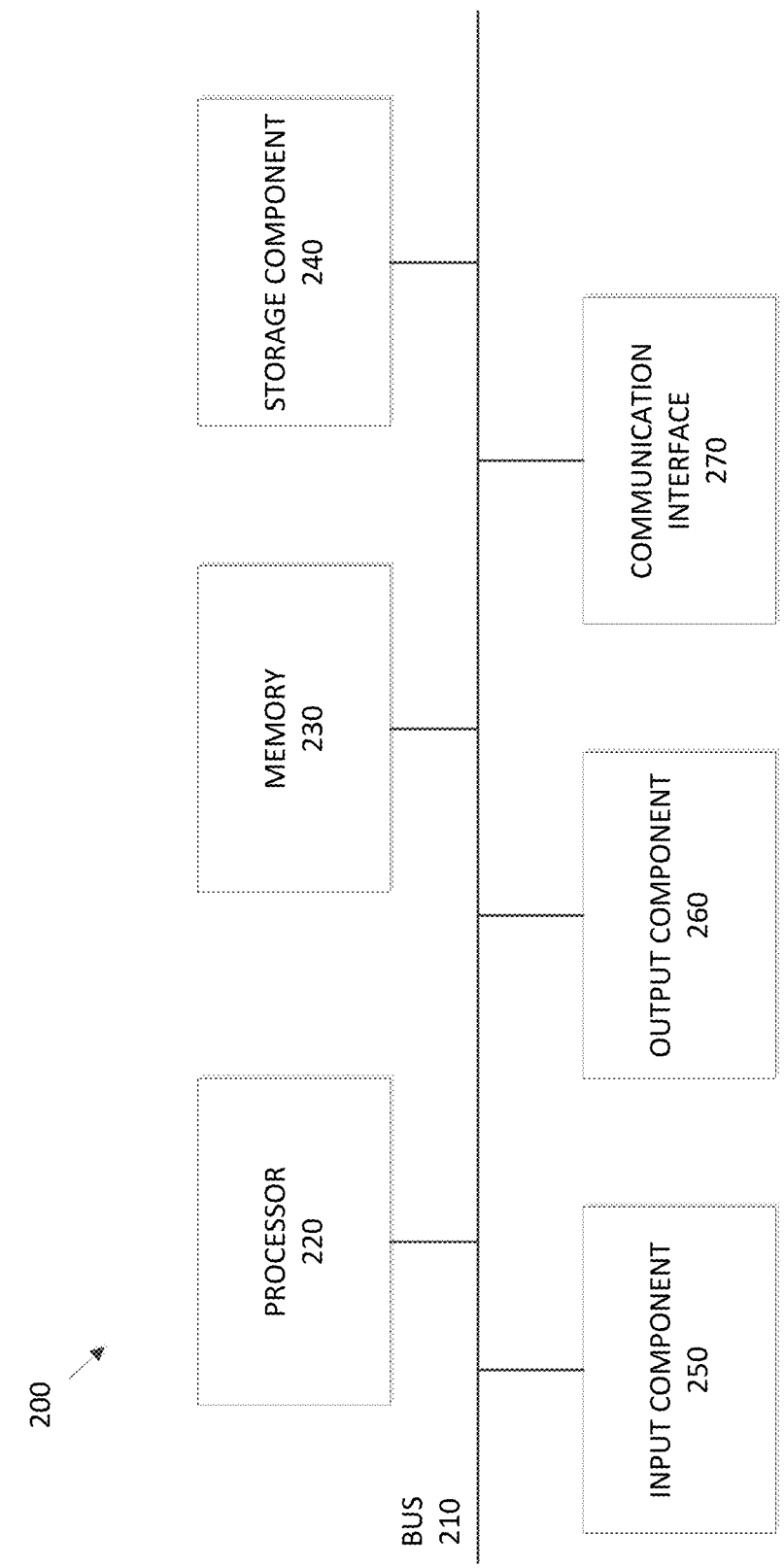
FIG. 2 is a diagram of example components of one or more devices of FIG. 1.

FIG. 2 is a diagram of example components of one or more devices of FIG. 1. A device 200 may correspond to user device 110 and/or platform 120. As shown in FIG. 2, device 200 may include a bus 210, a processor 220, a memory 230, a storage component 240, an input component 250, an output component 260, and a communication interface 270.

Bus 210 includes a component that permits communication among the components of device 200. Processor 220 is implemented in hardware, firmware, or a combination of hardware and software. Processor 220 is a central processing unit (CPU), a graphics processing unit (GPU), an accelerated processing unit (APU), a microprocessor, a microcontroller, a digital signal processor (DSP), a field-programmable gate array (FPGA), an application-specific integrated circuit (ASIC), or another type of processing component. In some implementations, processor 220 includes one or more processors capable of being programmed to perform a function. Memory 230 includes a random access memory (RAM), a read only memory (ROM), and/or another type of dynamic or static storage device (e.g., a flash memory, a magnetic memory, and/or an optical memory) that stores information and/or instructions for use by processor 220.

Storage component 240 stores information and/or software related to the operation and use of device 200. For example, storage component 240 may include a hard disk (e.g., a magnetic disk, an optical disk, a magneto-optic disk, and/or a solid state disk), a compact disc (CD), a digital versatile disc (DVD), a floppy disk, a cartridge, a magnetic tape, and/or another type of non-transitory computer-readable medium, along with a corresponding drive.

Input component 250 includes a component that permits device 200 to receive information, such as via user input (e.g., a touch screen display, a keyboard, a keypad, a mouse, a button, a switch, and/or a microphone). Additionally, or alternatively, input component 250 may include a sensor for sensing information (e.g., a global positioning system (GPS) component, an accelerometer, a gyroscope, and/or an actuator). Output component 260 includes a component that provides output information from device 200 (e.g., a display, a speaker, and/or one or more light-emitting diodes (LEDs)).

Communication interface 270 includes a transceiver-like component (e.g., a transceiver and/or a separate receiver and transmitter) that enables device 200 to communicate with other devices, such as via a wired connection, a wireless connection, or a combination of wired and wireless connections. Communication interface 270 may permit device 200 to receive information from another device and/or provide information to another device. For example, communication interface 270 may include an Ethernet interface, an optical interface, a coaxial interface, an infrared interface, a radio frequency (RF) interface, a universal serial bus (USB) interface, a Wi-Fi interface, a cellular network interface, or the like.

Device 200 may perform one or more processes described herein. Device 200 may perform these processes in response to processor 220 executing software instructions stored by a non-transitory computer-readable medium, such as memory 230 and/or storage component 240. A computer-readable medium is defined herein as a non-transitory memory device. A memory device includes memory space within a single physical storage device or memory space spread across multiple physical storage devices.

Software instructions may be read into memory 230 and/or storage component 240 from another computer-readable medium or from another device via communication interface 270. When executed, software instructions stored in memory 230 and/or storage component 240 may cause processor 220 to perform one or more processes described herein. Additionally, or alternatively, hardwired circuitry may be used in place of or in combination with software instructions to perform one or more processes described herein. Thus, implementations described herein are not limited to any specific combination of hardware circuitry and software.

The number and arrangement of components shown in FIG. 2 are provided as an example. In practice, device 200 may include additional components, fewer components, different components, or differently arranged components than those shown in FIG. 2. Additionally, or alternatively, a set of components (e.g., one or more components) of device 200 may perform one or more functions described as being performed by another set of components of device 200.

Figure 3:
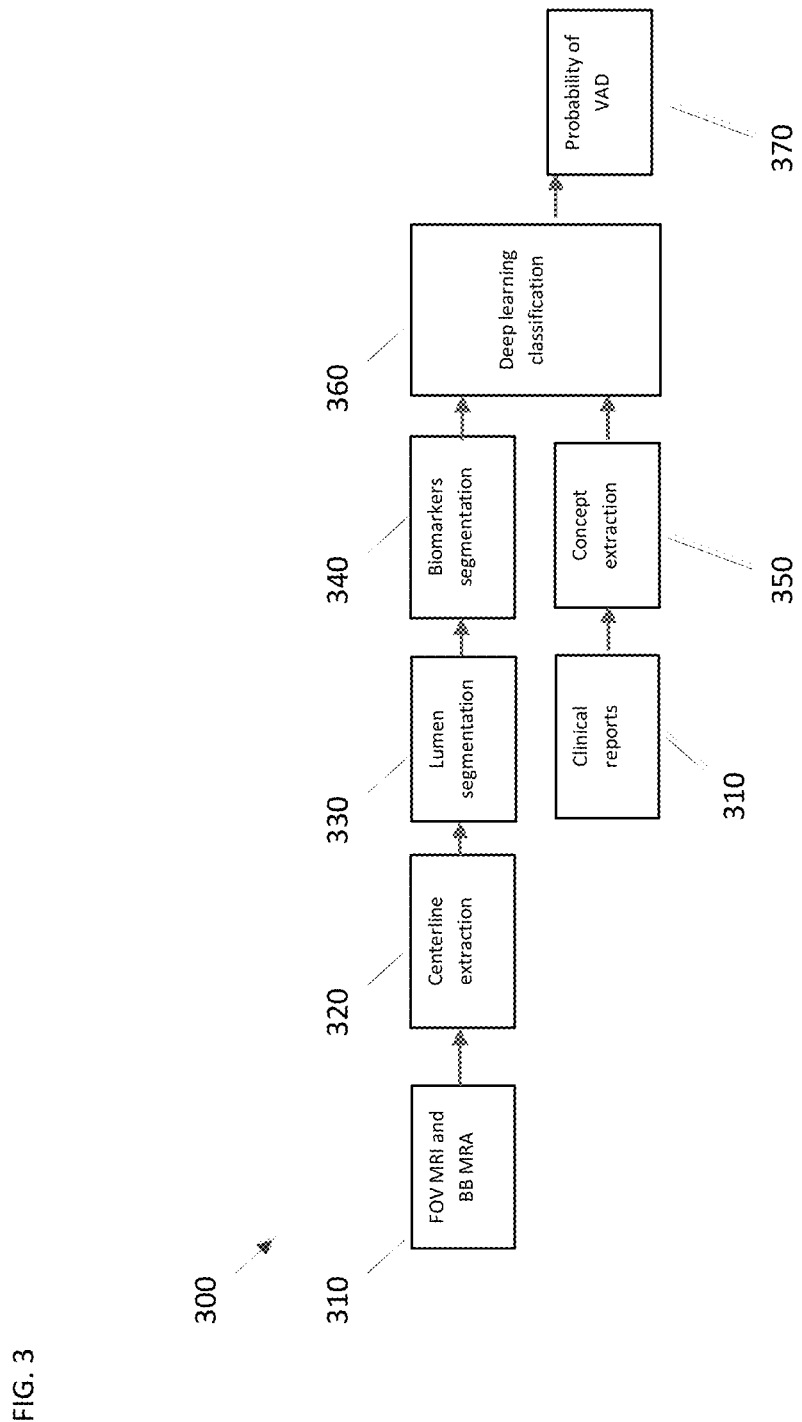
FIG. 3 is a flowchart of a method of determining a risk probability of vertebral artery dissection (VAD), according to embodiments.

FIG. 3 shows a flowchart of an example method 300 of predicting a probability of VAD. In some implementations, one or more process blocks of FIG. 3 may be performed by platform 120. In some implementations, one or more process blocks of FIG. 3 may be performed by another device or a group of devices separate from or including platform 120, such as user device 110.

As shown in FIG. 3, the method at operation 310 receives inputs from two sources: an image source and a text source. The images are fed into a process that includes three operations: centerline extraction operation 320, lumen segmentation operation 330, and biomarker quantification operation 340. At concept extraction operation 350, information such as, for example, a gender of the patient, a body mass index (BMI) of the patient, or a medication history of the patient, is extracted from the text input received from the text source.

Figure 4A:
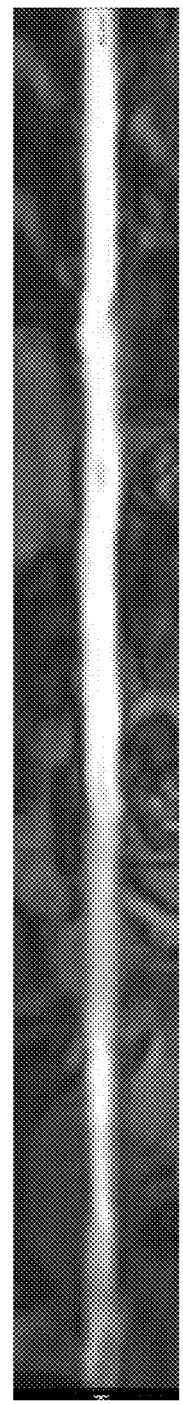
FIG. 4A is an example of a raw image of a vertebral artery segment, according to embodiments.
Figure 4B:
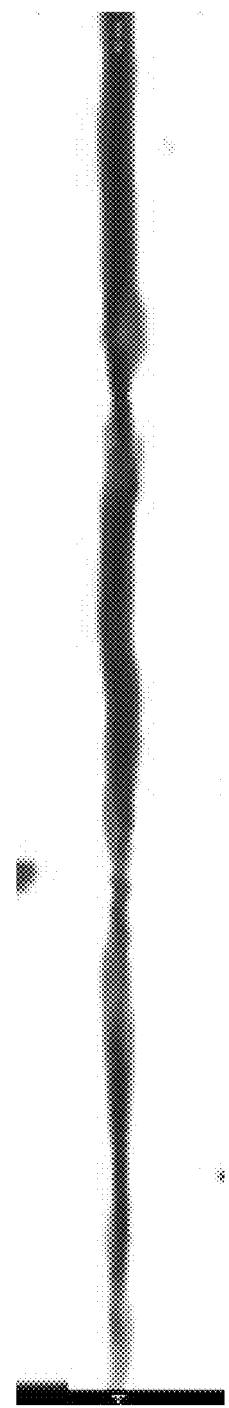
FIG. 4B is an example of a cost image in CMPR view created from a manual centerline.

In the analysis of image data, the centerline extraction operation 320 may include two stages: minimum cost path analysis stage and a refinement stage. The minimum cost path may be based on two inputs: 1) two manually annotated seed points indicating the beginning and the ending point of the vertebral artery segment, and 2) a cost image, such as for example the cost image shown in FIG. 4B, that has low response in the middle of the vessel.

Figure 5:
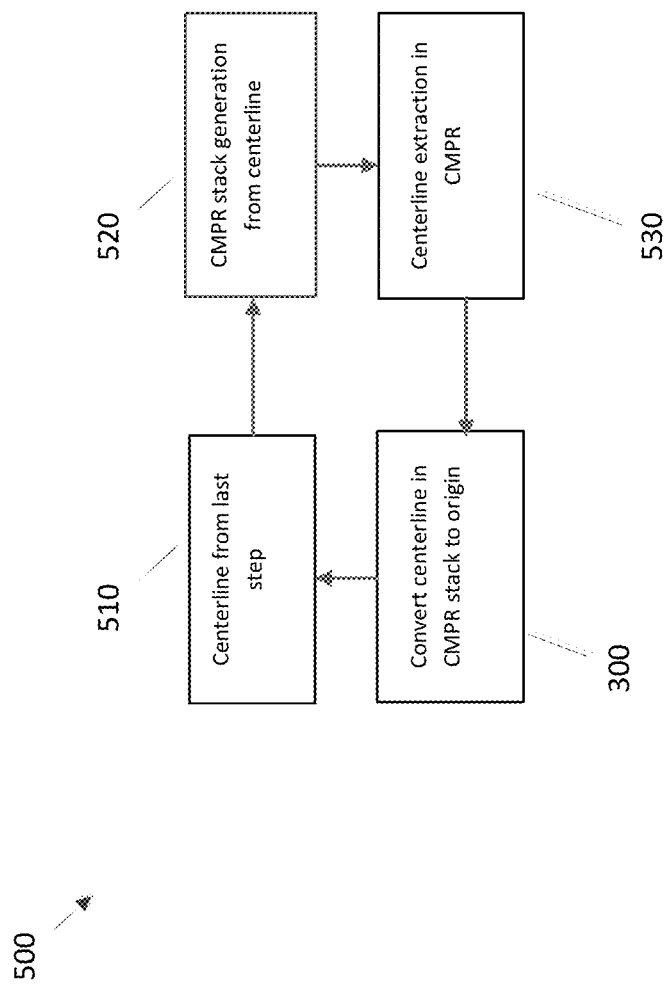
FIG. 5 is a flowchart of a method of refining a centerline, according to embodiments.
Figure 6:
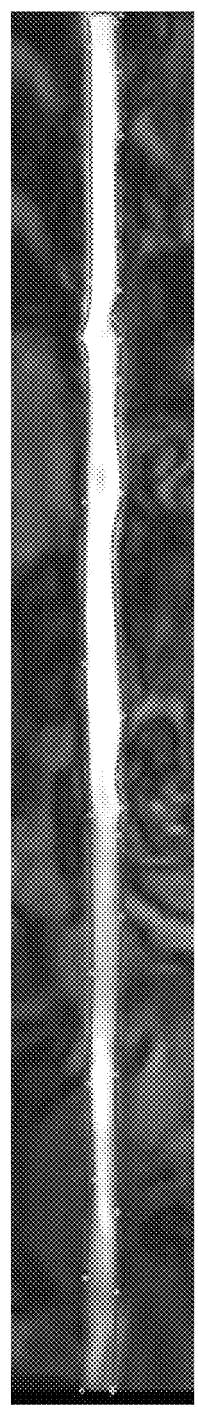
FIG. 6 is an example of a vessel lumen segmentation, according to embodiments.

The following refinement stage may be an iterative process, such as for example method 500 that is shown in FIG. 5. For example, an initial centerline extracted from the minimum cost path analysis stage at operation 510 may be used at operation 520 to generate a stack of curved multi plan reconstruction (CMPR) images. In the CMPR stack, which may be 3-dimensional, and in which the vessels may be less curved, minimum cost path analysis may be performed again at operation 530 to extract a centerline in the CMPR. At operation 540, the centerline in the CMPR may be converted back to the original image space to obtain a new centerline. These operations can be iterated, for example starting again at operation 510, until the centerline locates right in the vessel center.

The extracted and refined centerline may then be used as input for the lumen segmentation operation 330. From the centerline, a CMPR may be created again with a custom defined big resolution that is able to zoom into the vicinity of the centerline. In this way, the challenge raised by small vessel structure may be overcome. As an example, any supervised deep learning segmentation networks, such as VNet and 3D UNet, may learn the boundaries of the vertebral artery lumen.

In operation 340 shown in FIG. 3, biomarkers may be extracted from the extracted centerline and lumen.

In operation 350, different measures from patients such as body mass index, drug history and blood test results may be extracted from clinical reports using, for example, language processing techniques. The output from operations 340 and 350 are then used at operation 360 to train a deep learning classification model to predict development of VAD at operation 370.

In some embodiments, centerline extraction operation 320 may make use of other centerline extraction methods, such as adding shape information from atlases to increase successful rate in case of full occlusion.

In some embodiments, lumen segmentation operation 330 may make use of model-based unsupervised methods.

In some embodiments, the deep learning classification model can have different derivatives, such as AlexNet, Inception Net, Resnet of different layers as well as any other classification networks.

Figure 7:
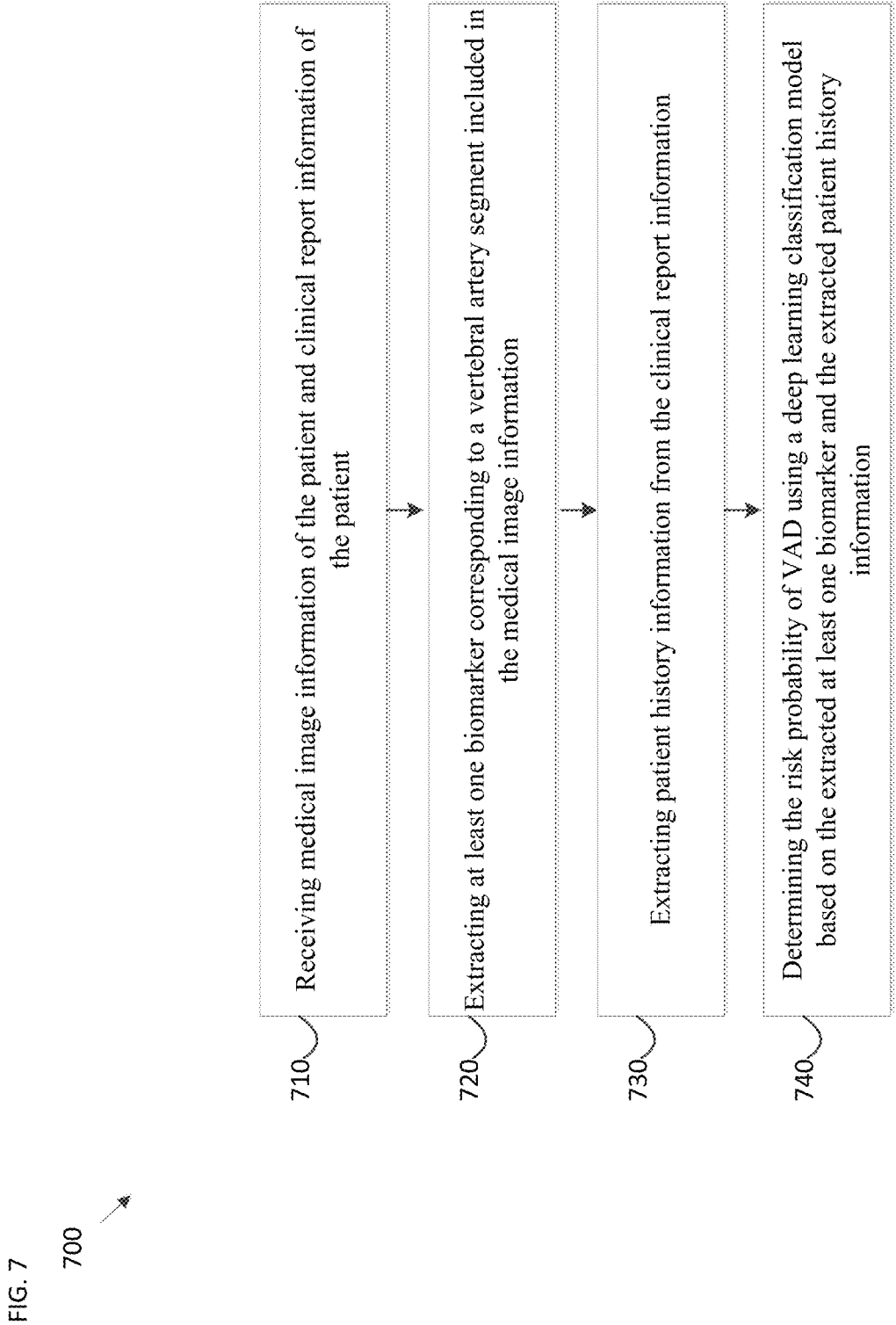
FIG. 7 is a flowchart of a method of determining a risk probability of vertebral artery dissection (VAD), according to embodiments

FIG. 7 is a flowchart of a method 700 for predicting a risk probability of VAD in a patient, according to embodiments. In some implementations, one or more process blocks of FIG. 7 may be performed by platform 120. In some implementations, one or more process blocks of FIG. 7 may be performed by another device or a group of devices separate from or including platform 120, such as user device 110. Some aspects of method 700 may correspond to aspects of method 300 discussed above.

As shown in FIG. 7, in operation 710, the method 700 includes receiving medical image information of the patient and clinical report information of the patient.

In operation 720, the method 700 includes extracting at least one biomarker corresponding to a vertebral artery segment included in the medical image information.

In operation 730, the method 700 includes extracting patient history information from the clinical report information.

In operation 740, the method 700 includes determining the risk probability of VAD using a deep learning classification model based on the extracted at least one biomarker and the extracted patient history information.

In embodiments, the extracting of the at least one biomarker may further include extracting a centerline of the vertebral artery segment, segmenting a lumen of the vertebral artery segment using the extracted centerline, and extracting the at least one biomarker based on the centerline and the lumen.

In embodiments, the extracting of the centerline may further include determining an initial centerline by performing a minimum cost path analysis, and refining the initial centerline to generate a refined centerline.

In embodiments, the minimum cost path analysis may be performed based on at least two seed points corresponding to the vertebral artery segment, and a cost image generated from the medical image information.

In embodiments, the at least two seed points may include a first seed point manually annotated at a beginning of the vertebral artery segment, and a second seed point manually annotated at an end of the vertebral artery segment.

In embodiments, the method 700 may further include generating a plurality of curved multi plan reconstruction (CMPR) images using the initial centerline, performing the minimum cost path analysis on the CMPR images to extract a revised centerline, and converting the revised centerline to an original image space of the medical image information to obtain the refined centerline.

In embodiments, the refined centerline may be used to generate a plurality of CMPR images, and the plurality of CMPR images may be used to segment the lumen.

In embodiments, the lumen may be segmented from the medical image information using a deep learning segmentation model.

In embodiments, the at least one biomarker may include at least one from among a geometry of the vertebral artery segment, a cervical distortion, and a stiffness of a vessel wall.

In embodiments, the patient history information may include at least from among a gender of the patient, a body mass index of the patient, a medication history of the patient, and a blood test result of the patient.

The foregoing disclosure provides illustration and description, but is not intended to be exhaustive or to limit the implementations to the precise form disclosed. Modifications and variations are possible in light of the above disclosure or may be acquired from practice of the implementations.

As used herein, the term component is intended to be broadly construed as hardware, firmware, or a combination of hardware and software.

It will be apparent that systems and/or methods, described herein, may be implemented in different forms of hardware, firmware, or a combination of hardware and software. The actual specialized control hardware or software code used to implement these systems and/or methods is not limiting of the implementations. Thus, the operation and behavior of the systems and/or methods were described herein without reference to specific software code—it being understood that software and hardware may be designed to implement the systems and/or methods based on the description herein.

Even though particular combinations of features are recited in the claims and/or disclosed in the specification, these combinations are not intended to limit the disclosure of possible implementations. In fact, many of these features may be combined in ways not specifically recited in the claims and/or disclosed in the specification. Although each dependent claim listed below may directly depend on only one claim, the disclosure of possible implementations includes each dependent claim in combination with every other claim in the claim set.

No element, act, or instruction used herein should be construed as critical or essential unless explicitly described as such. Also, as used herein, the articles "a" and "an" are intended to include one or more items, and may be used interchangeably with "one or more." Furthermore, as used herein, the term "set" is intended to include one or more items (e.g., related items, unrelated items, a combination of related and unrelated items, etc.), and may be used interchangeably with "one or more." Where only one item is intended, the term "one" or similar language is used. Also, as used herein, the terms "has," "have," "having," or the like are intended to be open-ended terms. Further, the phrase "based on" is intended to mean "based, at least in part, on" unless explicitly stated otherwise.

What is claimed is:

1. A method of determining a risk probability of vertebral artery dissection (VAD) in a patient, the method comprising:
    receiving, by at least one processor, medical image information of the patient and clinical report information of the patient;

extracting, by said at least one processor, at least one biomarker corresponding to a vertebral artery segment included in the medical image information, wherein the at least one biomarker is determined based on a centerline of the vertebral artery segment that is extracted from the medical image information, and a lumen of the vertebral artery segment that is segmented using the centerline;

extracting, by said at least one processor, patient history information from the clinical report information; and determining, by said at least one processor, the risk probability of VAD using a deep learning classification model based on the extracted at least one biomarker and the extracted patient history information.

2. The method of claim 1, wherein the extracting of the at least one biomarker further comprises:

extracting, by said at least one processor, the centerline of the vertebral artery segment;

segmenting, by said at least one processor, the lumen of the vertebral artery segment using the extracted centerline; and extracting, by said at least one processor, the at least one biomarker based on the centerline and the lumen.

3. The method of claim 2, wherein the extracting of the centerline further comprises:

determining, by said at least one processor, an initial centerline by performing a minimum cost path analysis; and refining, by said at least one processor, the initial centerline to generate a refined centerline.

4. The method of claim 3, wherein the minimum cost path analysis is performed, by said at least one processor, based on at least two seed points corresponding to the vertebral artery segment, and a cost image generated from the medical image information.

5. The method of claim 4, wherein the at least two seed points include a first seed point manually annotated at a beginning of the vertebral artery segment, and a second seed point manually annotated at an end of the vertebral artery segment.

6. The method of claim 3, further comprising:

generating, by said at least one processor, a plurality of curved multi plan reconstruction (CMPR) images using the initial centerline;

performing, by said at least one processor, the minimum cost path analysis on the CMPR images to extract a revised centerline; and converting, by said at least one processor, the revised centerline to an original image space of the medical image information to obtain the refined centerline.

7. The method of claim 3, wherein the refined centerline is used to generate a plurality of CMPR images, and wherein the plurality of CMPR images are used to segment the lumen.

8. The method of claim 3, wherein the lumen is segmented, by said at least one processor, from the medical image information using a deep learning segmentation model.

9. The method of claim 1, wherein the patient history information is extracted, by said at least one processor, from the clinical report information using a language model.

10. The method of claim 1, wherein the patient history information includes at least from among a gender of the patient, a body mass index of the patient, a drug history of the patient, and a blood test result of the patient.

11. A apparatus for determining a risk probability of vertebral artery dissection (VAD) in a patient, the apparatus comprising:

at least one memory configured to store program code; and at least one processor configured to read the program code and operate as instructed by the program code, the program code including:

receiving code configured to cause the at least one processor to receive medical image information of the patient and clinical report information of the patient;

first extracting code configured to cause the at least one processor to extract at least one biomarker corresponding to a vertebral artery segment included in the medical image information, wherein the at least one biomarker is determined based on a centerline of the vertebral artery segment that is extracted from the medical image information, and a lumen of the vertebral artery segment that is segmented using the centerline;

second extracting code configured to cause the at least one processor to extract patient history information from the clinical report information; and determining code configured to cause the at least one processor to determine the risk probability of VAD using a deep learning classification model based on the extracted at least one biomarker and the extracted patient history information.

12. The apparatus of claim 11, wherein the first extracting code further comprises:

third extracting code configured to cause the at least one processor to extract the centerline of the vertebral artery segment;

segmenting code configured to cause the at least one processor to segment the lumen of the vertebral artery segment using the extracted centerline;

fourth extracting code configured to cause the at least one processor to extract the at least one biomarker based on the centerline and the lumen.

13. The apparatus of claim 12, wherein the third extracting code further comprises:

initial centerline determining code configured to cause the at least one processor to determine an initial centerline by performing a minimum cost path analysis;

refining code configured to cause the at least one processor to refine the initial centerline to generate a refined centerline.

14. The apparatus of claim 13, wherein the minimum cost path analysis is performed based on at least two seed points corresponding to the vertebral artery segment, and a cost image generated from the medical image information.

15. The apparatus of claim 14, wherein the at least two seed points include a first seed point manually annotated at a beginning of the vertebral artery segment, and a second seed point manually annotated at an end of the vertebral artery segment.

16. The apparatus of claim 13, further comprising:

generating code configured to cause the at least one processor to generate a plurality of curved multi plan reconstruction (CMPR) images using the initial centerline;

analysis code configured to cause the at least one processor to perform the minimum cost path analysis on the CMPR images to extract a revised centerline; and converting code configured to cause the at least one processor to convert the revised centerline to an original image space of the medical image information to obtain the refined centerline.

17. The apparatus of claim 13, wherein the refined centerline is used to generate a plurality of CMPR images, and wherein the plurality of CMPR images are used to segment the lumen.

18. The apparatus of claim 13, wherein the lumen is segmented from the medical image information using a deep learning segmentation model.

19. The apparatus of claim 11, wherein the at least one biomarker includes at least one from among a geometry of the vertebral artery segment, a cervical distortion, and stiffness of a vessel wall.

20. A non-transitory computer-readable medium storing instructions that, when executed by at least one processor of a device for determining a risk probability of vertebral artery dissection (VAD) in a patient, cause the at least one processor to:

receive medical image information of the patient and clinical report information of the patient;

extract at least one biomarker corresponding to a vertebral artery segment included in the medical image information, wherein the at least one biomarker is determined based on a centerline of the vertebral artery segment that is extracted from the medical image information, and a lumen of the vertebral artery segment that is segmented using the centerline;

extract patient history information from the clinical report information; and determine the risk probability of VAD using a deep learning classification model based on the extracted at least one biomarker and the extracted patient history information.

* * * * *